United States Patent
Powell et al.

(10) Patent No.: US 9,435,785 B2
(45) Date of Patent: Sep. 6, 2016

(54) METHODS FOR ANALYZING CYSTEAMINE COMPOSITIONS

(71) Applicant: Raptor Pharmaceuticals Inc., Novato, CA (US)

(72) Inventors: Kathlene Powell, Cary, NC (US); Ramesh Muttavarapu, Durham, NC (US)

(73) Assignee: RAPTOR PHARMACEUTICALS INC., Novato, CA (US)

( * ) Notice: Subject to any disclaimer, the term of this patent is extended or adjusted under 35 U.S.C. 154(b) by 43 days.

(21) Appl. No.: 14/306,820

(22) Filed: Jun. 17, 2014

(65) Prior Publication Data
US 2015/0056712 A1 Feb. 26, 2015

Related U.S. Application Data

(60) Provisional application No. 61/835,987, filed on Jun. 17, 2013.

(51) Int. Cl.
| | |
|---|---|
| *G01N 33/15* | (2006.01) |
| *B01D 15/32* | (2006.01) |
| *G01N 21/33* | (2006.01) |
| *G01N 30/02* | (2006.01) |
| *G01N 30/06* | (2006.01) |
| *G01N 30/88* | (2006.01) |

(52) U.S. Cl.
CPC ............ *G01N 33/15* (2013.01); *B01D 15/325* (2013.01); *G01N 21/33* (2013.01); *G01N 30/02* (2013.01); *G01N 30/06* (2013.01); *G01N 2030/027* (2013.01); *G01N 2030/8818* (2013.01); *Y10T 436/173845* (2015.01)

(58) Field of Classification Search
CPC ...... G01N 33/15; G01N 30/02; G01N 30/06; G01N 2030/027
USPC ......... 436/106, 111, 119, 120, 161, 164, 171
See application file for complete search history.

(56) References Cited

U.S. PATENT DOCUMENTS

| | | | | |
|---|---|---|---|---|
| 4,507,500 | A * | 3/1985 | Nakayama | C07C 319/02 564/340 |
| 5,256,362 | A * | 10/1993 | Goto | B01J 2/22 264/13 |
| 7,947,742 | B2 * | 5/2011 | Batycky | A61K 9/0075 424/46 |
| 8,026,284 | B2 * | 9/2011 | Dohil | A61K 31/13 424/474 |
| 8,389,014 | B2 | 3/2013 | Longo et al. | |
| 2004/0076588 | A1 * | 4/2004 | Batycky | A61K 9/0075 424/46 |
| 2005/0250838 | A1 * | 11/2005 | Challapalli | A61K 9/2031 514/419 |

(Continued)

FOREIGN PATENT DOCUMENTS

| | | |
|---|---|---|
| CN | 103018359 A | 4/2013 |
| WO | WO-2007/089670 A2 | 8/2007 |

OTHER PUBLICATIONS

Allison, L. A. et al, Journal of Liquid Chromatography 1983, 6, 1785-1798.*

(Continued)

*Primary Examiner* — Arlen Soderquist
(74) *Attorney, Agent, or Firm* — Marshall, Gerstein & Borun LLP

(57) ABSTRACT

Methods of analyzing purity of compositions comprising cysteamine and detecting impurities in cysteamine compositions are described.

18 Claims, 3 Drawing Sheets

(56) References Cited

U.S. PATENT DOCUMENTS

| | | | |
|---|---|---|---|
| 2008/0103169 A1* | 5/2008 | Phillips | A61J 1/20 514/303 |
| 2008/0200651 A1* | 8/2008 | Ostergaard | C07K 1/113 530/383 |
| 2008/0206883 A1 | 8/2008 | Black | |
| 2009/0076166 A1* | 3/2009 | Dohil | A61K 31/145 514/665 |
| 2010/0069482 A1* | 3/2010 | Longo | A61K 9/0048 514/458 |
| 2012/0178900 A1 | 7/2012 | Dave et al. | |
| 2014/0370085 A1* | 12/2014 | Powell | A61K 9/5026 424/458 |

OTHER PUBLICATIONS

Biffar, S. et al, Journal of Chromatography 1985, 318, 404-407.*
Kelly, M. J. et al, Biomedical Chromatography 1987, 2, 216-220.*
Garcia, R. A. G. et al, Analytical Biochemistry 1988, 170, 432-440.*
Yamashita, G. T. et al, JOurnal of Chromatography 1989, 491, 341-354.*
Patel, N. et al, Chemical Research in Toxicology 1991, 4, 421-426.*
Jayatilleke, E. et al, Analytical Biochemistry 1993, 214, 452-457.*
Wakabayashi, H. et al, Journal of Pharmaceutical & Biomedical Analysis 1994, 12, 1147-1152.*
Winters, R. A, et al, Analytical Biochemistry 1995, 227, 14-21.*
Liu, S. et al, Current Eye Research 1996, 15, 726-732.*
Favaro, G. et al, Analytica Chimica Acta 1996, 332, 249-255.*
Lakritz, J. et al, Analytical Biochemistry 1997, 247, 63-68.*
Pastore, A. et al, Clinical Chemistry 1998, 44, 825-832.*
Stachwicz, M. et al, Journal of Pharmaceutical and Biomedical Analysis 1998, 17, 767-773.*
Accinni, R. et al, Journal of Chromatography A 1998, 828, 397-400.*
Martin, S. C. et al, Clinical Chemistry 1999, 45, 150-152.*
Wollard, D. C. et al, Food Chemistry 2000, 69, 201-208.*
Afzal, M. et al, in "Methods in Molecular Biology: Oxidative Stress Biomarkers and Antioxidant Protocols" 2002, vol. 186, pp. 117-122, Edited by D. Armstrong, Humana Press Inc., Totowa, NJ.*
Vignaud, C. et al, Journal of Chromatography A 2004, 1031, 125-133.*
Kusmierek, K. et al, Analytical and Bioanalytical Chemistry 2005 382, 231-233.*
Pinto, J. T. et al, Journal of Neurochemistry, 2005, 94, 1087-1101.*
Barayni, M. et al, Journal of Chromatography A 2006, 1120, 13-20.*
Huang, Y.-B. et al, Phytochemical Analysis 2006, 17, 439-446.*
Lahiani-Skiba, M. et al, Journal of Inclusion Phenomena and Macrocyclic Chemistry 2007, 57, 211-217.*
Santagati, N. A. et al, Journal of Chromatographic Science 2008, 46, 150-156.*
Kusmierek, K. et al, Journal of Chromatography B 2009, 877, 3300-3308.*
Pinto, J. T. et al, Journal of Chromatography B 2009, 877, 3434-3441.*
Dutov, A. A. et a, Biomeditsinskaia Khimiia 201, 56, 609-615.*
Ozyurek, M. et al, Analytica Chimica Acta 2012, 750, 173-181.*
Dohil et al., Understanding intestinal cysteamine bitartrate absorption, J. Pediatr., 148(6):764-9 (2006).
Gahl et al., Cystinosis, N. Engl. J. Med., 347(2):111-21 (2002).
International Search Report and Written Opinion, corresponding International Application No. PCT/US14/42616, mailed Oct. 9, 2014.
Min-Oo et al., Cysteamine, the molecule used to treat cystinosis, potentiates the antimalarial efficacy of artemisinin, Antimicrob. Agents Chemother., 54(8):3262-70 (2010).
Moldoveanu et al., Sample Preparation in Chromatography, Amsterdam, The Netherlands: Elsevier Science B.V., p. 225 (2002).
Ogony et al., High performance liquid chromatography analysis of 2-mercaptoethylamine (cysteamine) in biological samples by derivatization with N-(1-pyrenyl) maleimide (NPM) using fluorescence detection, J. Chromatogr. B Analyt. Technol. Biomed. Life Sci., 843(1):57-62 (2006).

* cited by examiner

US 9,435,785 B2

METHODS FOR ANALYZING CYSTEAMINE COMPOSITIONS

The present invention claims the priority benefit of U.S. Provisional Patent Application No. 61/835,987 filed Jun. 17, 2013, herein incorporated by reference.

FIELD OF THE INVENTION

The invention relates generally to methods for analyzing purity of compositions comprising cysteamine and detecting impurities in cysteamine compositions.

BACKGROUND

Cysteamine ($HS-CH_2-CH_2-NH_2$) is able to cross cell membranes easily due to its small size. At present, cysteamine is FDA-approved for the treatment of cystinosis, an intra-lysosomal cystine storage disorder. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Treatment with cysteamine has been shown to result in lowering of intracellular cystine levels in circulating leukocytes (Dohil et al., J. Pediatr 148(6):764-9, 2006).

Impurities can be present in cysteamine formulations due to byproduct formation during the manufacturing process and/or due to modification (e.g., degradation) during storage of the drug product. Accurate and complete determination of the purity of cysteamine-containing formulations is important in securing marketing approval for the pharmaceutical product and in demonstrating that the pharmaceutical product has acceptable impurity levels for human administration at the time of release and that it has acceptable storage stability. Analysis of the purity of cysteamine-containing formulations using an HPLC method with an electrochemical detection system has proven not to have the sensitivity required to detect certain impurities found in cysteamine formulations.

The present invention provides improved methods for analyzing purity of compositions comprising cysteamine and detecting impurities in cysteamine compositions.

SUMMARY

The invention is directed to a method of analyzing purity of compositions comprising cysteamine. The method comprises injecting a sample solution comprising cysteamine onto a reverse-phase HPLC column; eluting the sample from the column using a mobile phase comprising an alkyl sulfonic acid (e.g., 1-hexanesulfonic acid and/or 1-octanesulfonic acid), a buffer, acetonitrile, and methanol; and measuring the eluted sample using a UV detector. The eluted sample is measured at a wavelength of about 170 nm to about 250 nm.

In related methods, the invention provides a method of analyzing purity of delayed-release cysteamine formulations, such as enteric-coated cysteamine beads. Such beads include beads loaded in individual-dose capsules that are formulated for oral administration to a patient. The method comprises grinding enteric-coated cysteamine beads; dissolving the ground beads in a solvent having an acidic pH to form a sample solution comprising cysteamine; injecting the sample solution onto a reverse-phase HPLC column; eluting the sample from the column using a mobile phase comprising an alkyl sulfonic acid (e.g., 1-hexanesulfonic acid and/or 1-octanesulfonic acid), a buffer, acetonitrile, and methanol; and measuring the eluted sample using a UV detector at a wavelength of about 170 nm to about 250 nm.

Additionally, the invention provides a method of analyzing purity of compositions comprising cysteamine comprising (i) dissolving a cysteamine sample in a solvent having an acidic pH to form a sample solution comprising cysteamine; (ii) injecting the sample solution onto a C18 reverse-phase HPLC column; (iii) gradient eluting the sample from the column using first and second mobile phases, wherein the first mobile phase comprises about 85% by volume of an aqueous solution having a pH of about 2.6, the aqueous solution comprising about 23.6 mM 1-octanesulfonic acid sodium and about 29 mM sodium phosphate; about 3% by volume of acetonitrile; and about 12% by volume of methanol, and the second mobile phase comprises about 10% by volume of an aqueous solution having a pH of about 2.6, the aqueous solution comprising about 0.2 M 1-octanesulfonic acid sodium and about 0.1 M sodium phosphate; about 18% by volume of acetonitrile; and about 72% by volume of methanol; and (iv) measuring the eluted sample using a UV detector at a wavelength of about 210 nm or less.

Further aspects of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to specific embodiments described herein. The entire document is intended to be related as a unified disclosure, and it should be understood that all combinations of features described herein are contemplated, even if the combination of features are not found together in the same sentence, or paragraph, or section of this document. For example, where embodiments concerning a method of analyzing purity of compositions comprising cysteamine are described, embodiments involving methods of analyzing delayed release cysteamine formulations such as enteric-coated cysteamine, and the like that have the same properties and features are specifically contemplated, and the reverse also is true.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to elements described as a selection within a range, it should be understood that all discrete subunits within the range are contemplated as an embodiment of the invention. Ranges may be expressed herein as from "about" or "approximately" one particular value and/or to "about" or "approximately" another particular value. When such a range is expressed, another embodiment according to the invention includes from the one particular value and/or to the other particular value. Similarly, when particular values are expressed as approximations, but use of antecedents such as "about," "at least about," or "less than about," it will be understood that the particular value forms another embodiment.

With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

DETAILED DESCRIPTION

Figure 1:
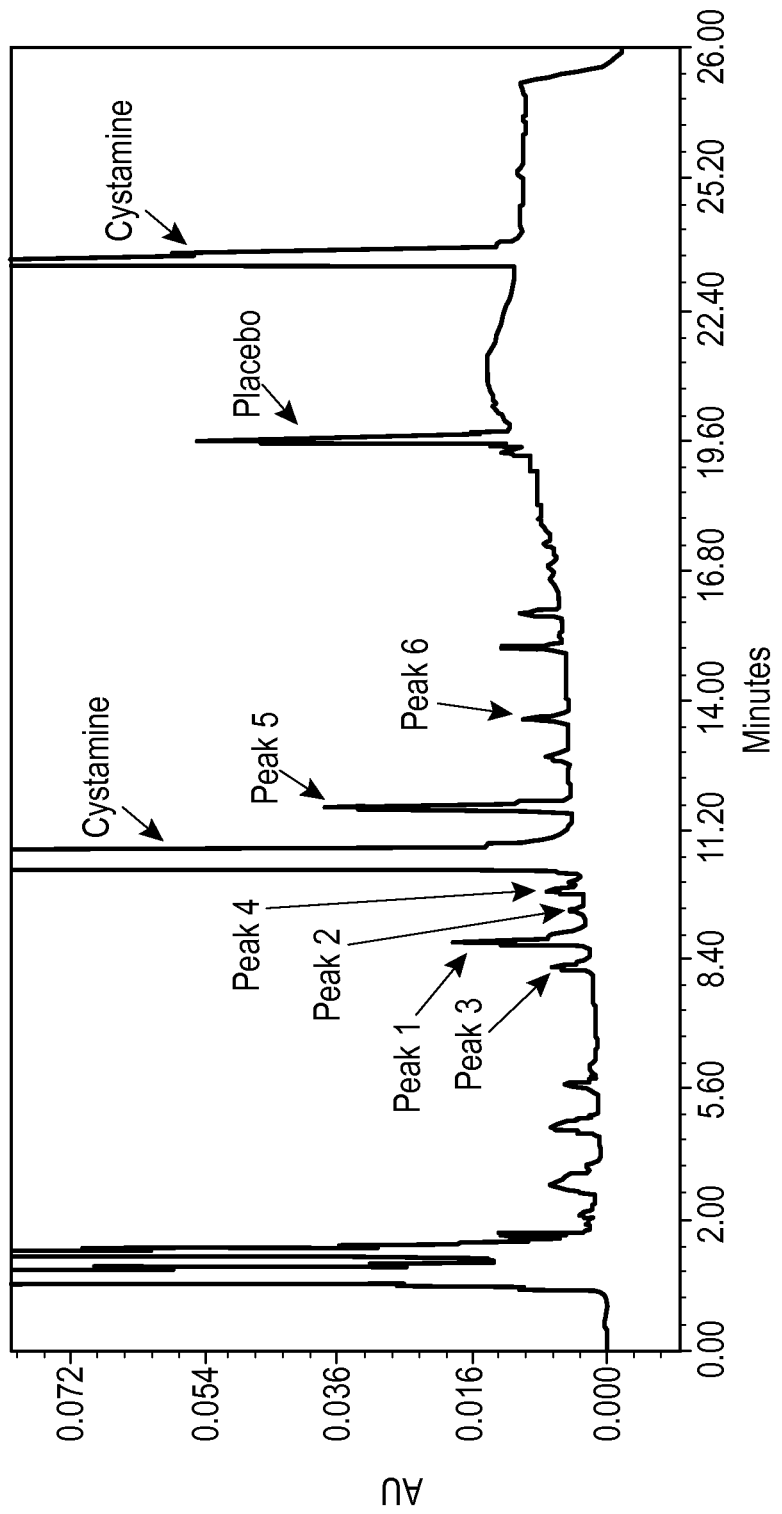
FIG. 1 provides an HPLC chromatogram of cysteamine obtained according to the methods described herein.

The invention provides improved methods for analyzing purity of compositions comprising cysteamine and detecting impurities in cysteamine compositions. Such methods preferably provide higher sensitivity and less selectivity relative to methods not in accordance with the invention. By providing less selectivity, the inventive methods allow detection of additional impurities than are detected by more selective methods. Thus, the inventive methods can provide a more complete and more accurate determination of the number and amounts of impurities and/or related substances present in a cysteamine formulation. As used herein, the term "cysteamine formulation," "cysteamine composition" or "composition comprising cysteamine" refers to any formulation comprising cysteamine, including formulations comprising cysteamine salts. As used herein, the term "related substances" refers to compounds derived from cysteamine that are present in the cysteamine formulation initially upon preparation and/or after storage. Cysteamine related substances include, but are not limited to, cysteamine dimer (i.e., cystamine) and other products obtained by modification of cysteamine and/or reaction of cysteamine with other components present in the formulation such as salts.

The invention is described in further detail below. Section headings are for convenience of reading and not intended to be limiting per se.

HPLC Methods

In one aspect, the invention provides a method for analyzing purity of compositions comprising cysteamine and detecting impurities in cysteamine compositions. The method comprises: injecting a sample solution comprising cysteamine onto a reverse-phase HPLC column; eluting the sample from the column using a mobile phase comprising an alkyl sulfonic acid, a buffer, acetonitrile, and methanol; and measuring the eluted sample using a UV detector at a wavelength of about 170 nm to about 250 nm. Optionally, the method includes dissolving a cysteamine sample in a solvent having an acidic pH to form the sample solution comprising cysteamine.

In a related aspect, the invention provides a method for analyzing purity of enteric-coated cysteamine beads and detecting impurities in enteric-coated cysteamine beads. The method comprises: grinding enteric-coated cysteamine beads; dissolving the ground beads in a solvent having an acidic pH to form a sample solution comprising cysteamine; injecting the sample solution onto a reverse-phase HPLC column; eluting the sample from the column using a mobile phase comprising 1-octanesulfonic acid, a buffer, acetonitrile, and methanol; and measuring the eluted sample using a UV detector.

In various embodiments, the solvent in which the cysteamine sample is dissolved comprises an alkyl sulfonic acid, a buffer, acetonitrile, and methanol. Exemplary solvents include the HPLC mobile phase. When the sample is gradient eluted using first and second mobile phases, the solvent is typically the mobile phase having the higher volume percentage of aqueous components and the lower volume percentage of organic components (generally referred to as the first mobile phase or mobile phase A).

The sample solution is injected onto a reverse-phase HPLC column. Typically, the sample solution is injected in a volume of 10 µL or 100 µL, however, other injection volumes can be used (e.g., 5 µL, 20 µL, 30 µL, 40 µL, 50 µL, 60 µL, 70 µL, 80 µL, or 90 µL of sample solution) and multiple injections may be used (e.g., two, three, four, or five injections of 10 µL of sample solution). A sufficient amount of sample is injected onto the column such that substances related to cysteamine may be detected. Generally, the amount of cysteamine injected onto the column is at least 30 µg, at least 40 µg, at least 50 µg, and/or at least 60 µg.

The HPLC column includes a packing material (i.e., a stationary phase). In reverse-phase HPLC, the column contains a hydrophobic packing material. Exemplary reverse phase HPLC columns include, but are not limited to, a C18 column, a C8 column, a silica column, a cyano-bonded silica column, and a phenyl-bonded silica column. The HPLC column generally has a packing material particle size of about 1 µm to about 10 µm in diameter, about 1 µm to about 7 µm in diameter, about 2 µm to about 5 µm in diameter, about 3 µm to about 4 µm in diameter, and/or about 3.5 µm in diameter. Typical HPLC columns have an internal diameter of about 0.1 mm to about 10 mm, about 0.1 mm to about 7 mm, about 0.15 mm to about 5 mm, about 0.3 mm to about 5 mm, about 0.5 mm to about 5 mm, about 0.7 mm to about 5 mm, about 1 mm to about 5 mm, about 1.5 mm to about 5 mm, about 2 mm to about 5 mm, about 3 mm to about 5 mm, about 4 mm to about 5 mm, and/or about 4.6 mm. Generally, HPLC columns have a length of about 5 mm to about 500 mm, about 10 mm to about 250 mm, about 20 mm to about 250 mm, about 30 mm to about 250 mm, about 50 mm to about 250 mm, about 75 mm to about 200 mm, and/or about 100 mm to about 150 mm.

Commercial HPLC columns include XBRIDGE analytical columns (Waters, Milford, Mass.), for example, XBRIDGE analytical columns having an internal diameter and a length, respectively, of 1.0×50 mm, 1.0×100 mm, 1.0×150 mm, 2.1×10 mm, 2.1×10 mm, 2.1×20 mm, 2.1×30 mm, 2.1×50 mm, 2.1×75 mm, 2.1×100 mm, 2.1×150 mm, 3.0×20 mm, 3.0×30 mm, 3.0×50 mm, 3.0×75 mm, 3.0×100 mm, 3.0×150 mm, 4.6×20 mm, 4.6×30 mm, 4.6×50 mm, 4.6×75 mm, 4.6×100 mm, 4.6×100 mm, 4.6×150 mm, and 4.6×250 mm. XBRIDGE analytical columns contain packing material having particle sizes, for example, of about 2.5 µm in diameter, about 3.5 µm in diameter, and about 5 µm in diameter.

The sample is eluted from the column using a mobile phase comprising an alkyl sulfonic acid, a buffer, acetonitrile, and methanol. Typically, the elution is a gradient elution. During a gradient elution, first and second mobile phases having different compositions are used. The first and second mobile phases are mixed in changing ratios throughout the elution such that the composition of the mobile phase changes over the course of the elution. A gradient elution optionally includes one or more stepped changes in the ratio of the mobile phases.

An aqueous solution comprising an alkyl sulfonic acid and a buffer typically is included in the mobile phase in an amount of about 5% to about 95% by volume of the mobile phase, for example, about 10% to about 90% by volume, about 15% to about 85% by volume, about 20% to about 80% by volume, about 25% to about 75% by volume, about 30% to about 70% by volume, about 35% to about 65% by volume, about 40% to about 60% by volume, and/or about 45% to about 55% by volume. Other amounts of the aqueous solution may also be used. For example, when the sample is gradient eluted, one mobile phase may include the aqueous solution at a lower concentration and the second mobile phase may include the aqueous solution at a higher concentration. Thus, other exemplary amounts of aqueous solution include about 75% to about 95% by volume, about 80% to about 90% by volume, about 85% by volume, about 5% to about 30% by volume, about 5% to about 25% by volume, about 5% to about 20% by volume, and/or about 5% to about 10% by volume. The aqueous solution typically has an acidic pH, for example a pH of about 1.5 to about 6.5, about 2 to about 6, about 2 to about 5, about 2 to about 4, about 2 to about 3, and/or about 2.4 to about 2.8.

Suitable alkyl sulfonic acids include, but are not limited to, ethanesulfonic acid, propanesulfonic acid, butanesulfonic acid, pentanesulfonic acid, hexanesulfonic acid, heptanesulfonic acid, octanesulfonic acid, nonanesulfonic acid, and decanesulfonic acid. The alkyl sulfonic acid (e.g., 1-hexanesulfonic acid or 1-octanesulfonic acid) may be included in the aqueous solution of the mobile phase in any of its salt forms such as in a sodium salt form, for example, 1-hexanesulfonic acid sodium or 1-octanesulfonic acid sodium. The alkyl sulfonic acid (or a salt thereof) typically is included in the aqueous solution at a concentration of about 15 mM to about 300 mM, about 20 mM to about 200 mM, about 30 mM to about 150 mM, about 40 mM to about 120 mM, about 50 mM to about 100 mM, and/or about 60 mM to about 90 mM. Other concentrations of the alkyl sulfonic acid (or salts thereof) may also be used. For example, when the sample is gradient eluted, one mobile phase may include the alkyl sulfonic acid (or salts thereof) at a lower concentration and the second mobile phase may include the alkyl sulfonic acid (or salts thereof) at a higher concentration. Thus, other exemplary concentrations of the alkyl sulfonic acid (or salts thereof) in the aqueous solution include about 15 mM to about 50 mM, about 15 mM to about 40 mM, about 20 mM to about 30 mM, about 100 mM to about 300 mM, about 120 mM to about 280 mM, and/or about 150 mM to about 250 mM.

A buffer typically is included in the aqueous solution at a concentration of about 15 mM to about 200 mM, 20 mM to about 150 mM, and/or 30 mM to about 100 mM. Other concentrations of buffer may also be used. For example, when the sample is gradient eluted, one mobile phase may include the buffer at a lower concentration and the second mobile phase may include the buffer at a higher concentration. Thus, other exemplary concentrations of buffer in the aqueous solution include about 15 mM to about 100 mM, about 20 mM to about 75 mM, about 25 mM to about 50 mM, about 75 mM to about 125 mM, about 85 mM to about 115 mM, about 100 mM to about 200 mM, and/or about 100 mM to about 150 mM. Exemplary buffers include any buffer having a $pK_a$ at an acidic pH, for example, a pH of about 1.5 to about 6, about 2 to about 5, about 2 to about 4, about 2 to about 3, and/or about 2 to about 2.5. Exemplary buffers include, but are not limited to, phosphate, citric acid/citrate, acetic acid/acetate, glycine, formic acid/formate, and succinic acid/succinate. In various embodiments, the buffer includes sodium phosphate.

Acetonitrile typically is included in the mobile phase in an amount of about 5% to about 95% by volume of the mobile phase, for example, about 1% to about 30% by volume, about 2% to about 25% by volume, about 3% to about 20% by volume, about 5% to about 15% by volume, about 8% to about 12% by volume, and/or about 10% by volume. Other amounts of acetonitrile may also be used. For example, when the sample is gradient eluted, one mobile phase may include acetonitrile at a lower concentration and the second mobile phase may include acetonitrile at a higher concentration. Thus, other exemplary amounts of acetonitrile include about 1% to about 8% by volume, about 1% to about 6% by volume, about 1% to about 5% by volume, about 2% to about 4% by volume, about 3% by volume, about 8% to about 30% by volume, about 10% to about 25% by volume, about 15% to about 20% by volume and/or about 18% by volume.

Methanol typically is included in the mobile phase in an amount of about 5% to about 85% by volume of the mobile phase, for example, about 10% to about 80% by volume, about 15% to about 75% by volume, about 20% to about 70% by volume, about 25% to about 65% by volume, about 30% to about 60% by volume, and/or about 35% to about 55% by volume. Other amounts of methanol may also be used. For example, when the sample is gradient eluted, one mobile phase may include methanol at a lower concentration and the second mobile phase may include methanol at a higher concentration. Thus, other exemplary amounts of methanol include about 5% to about 20% by volume, about 8% to about 15% by volume, about 12% by volume, about 50% to about 85% by volume, about 60% to about 80% by volume, and/or about 72% by volume.

An exemplary mobile phase comprises about 5% to about 95% by volume of an aqueous solution having a pH of about 2.0 to 3.0, the aqueous solution comprising an alkyl sulfonic acid (e.g., 1-hexanesulfonic acid and/or 1-octanesulfonic acid) and a phosphate buffer, about 1% to about 30% by volume of acetonitrile, and about 5% to about 85% by volume of methanol. In various embodiments, the aqueous solution includes about 15 mM to about 300 mM of an alkyl sulfonic acid (e.g., 1-hexanesulfonic acid and/or 1-octanesulfonic acid), and about 15 mM to about 200 mM phosphate buffer.

The sample can be gradient eluted using first and second mobile phases that are mixed in different ratios throughout the elution. An exemplary first mobile phase comprises about 75% to about 95% by volume of an aqueous solution having a pH of about 2.0 to 3.0, the aqueous solution comprising an alkyl sulfonic acid (e.g., 1-hexanesulfonic acid and/or 1-octanesulfonic acid) and a phosphate buffer, about 1% to about 8% by volume of acetonitrile, and about 5% to about 20% by volume of methanol. In various embodiments, the aqueous solution of the first mobile phase includes about 15 mM to about 50 mM of an alkyl sulfonic acid (e.g., 1-hexanesulfonic acid and/or 1-octanesulfonic acid), and about 15 mM to about 100 mM phosphate buffer. An exemplary second mobile phase comprises about 5% to about 30% by volume of an aqueous solution having a pH of about 2.0 to 3.0, the aqueous solution comprising an alkyl sulfonic acid (e.g., 1-hexanesulfonic acid and/or 1-octanesulfonic acid) and a phosphate buffer, about 8% to about 30% by volume of acetonitrile, and about 50% to about 85% by volume of methanol. In various embodiments, the aqueous solution of the second mobile phase includes about 100 mM to about 300 mM of an alkyl sulfonic acid (e.g., 1-hexanesulfonic acid and/or 1-octanesulfonic acid), and about 100 mM to about 200 mM phosphate buffer.

In a gradient elution, the gradient typically starts with a high percentage of the first mobile phase, for example, about 100% of the first mobile phase and 0% of the second mobile phase, about 90% of the first mobile phase and about 10% of the second mobile phase, and/or about 80% of the first mobile phase and about 20% of the second mobile phase. Over a period of time, for example, over at least 5 minutes, over at least 10 minutes, over at least 15 minutes, over at least 20 minutes, over at least 25 minutes, and/or over at least 30 minutes, the ratio of the first mobile phase to the second mobile phase is continuously decreased. At the end of the period of time, the percentage of the first mobile phase is lower than at the start of the gradient, for example, about 30% of the first mobile phase and about 70% of the second mobile phase, about 40% of the first mobile phase and about 60% of the second mobile phase, about 50% of the first mobile phase and about 50% of the second mobile phase, about 60% of the first mobile phase and about 40% of the second mobile phase, and/or about 70% of the first mobile phase and about 30% of the second mobile phase. In an exemplary elution at a flow rate of 1 mL/min, the elution profile provides 100% of the first mobile phase for 2 minutes, then linearly decreases the amount of the first mobile phase to 60% and linearly increases the amount of the second mobile phase to 40% over a period of 18 minutes, then provides 60% of the first mobile phase and 40% of the second mobile phase for 5 minutes, and then provides 100% of the first mobile phase for 15 minutes.

The sample is eluted from the column using a suitable flow rate, for example, about 0.001 mL/min to about 2 mL/min, about 0.01 mL/min to about 2 mL/min, about 0.1 mL/min to about 2 mL/min, about 0.5 mL/min to about 2 mL/min, and/or about 1 mL/min. Further, the sample is eluted at a suitable column temperature, for example, about 20° C. to about 80° C., about 25° C. to about 60° C., about 30° C. to about 50° C., and/or about 40° C.

The eluted sample is measured using a UV detector and the signal is recorded using a suitable recording device. Typically, the eluted sample is measured at a wavelength of about 170 nm to about 250 nm, about 170 nm to about 240 nm, about 170 nm to about 230 nm, about 170 nm to about 220 nm, about 170 nm to about 210 nm, 180 nm to about 250 nm, about 180 nm to about 240 nm, about 180 nm to about 230 nm, about 180 nm to about 220 nm, about 180 nm to about 210 nm, about 190 nm to about 250 nm, about 190 nm to about 240 nm, about 190 nm to about 230 nm, about 190 nm to about 220 nm, about 190 nm to about 210 nm, about 200 nm to about 250 nm, about 200 nm to about 240 nm, about 200 nm to about 230 nm, about 200 nm to about 220 nm, about 200 nm to about 210 nm, about 250 nm or less, about 240 nm or less, about 230 nm or less, about 220 nm or less, and/or about 210 nm or less.

Cysteamine Processing

The cysteamine formulation for analysis according to the inventive methods includes all forms of cysteamine, including pharmaceutically acceptable salts. A "pharmaceutically acceptable salt" is a salt that can be formulated into a compound for pharmaceutical use, including but not limited to metal salts (e.g., sodium, potassium, magnesium, calcium, etc.) and salts of ammonia or organic amines. Examples of cysteamine derivatives include hydrochloride, hydrobromide, acetate, maleate, pamoate, phosphate, methanesulfonate, p-toluenesulfonate, bitartrate and phosphocysteamine derivatives. An exemplary form of cysteamine is cysteamine bitartrate.

The cysteamine formulation can be an immediate release formulation. Immediate release formulations generally can be prepared for analysis by dissolving in a suitable solvent to form a sample solution. If needed, the immediate release cysteamine formulation can be ground or otherwise deaggregated prior to dissolving. If the cysteamine formulation is present in a capsule or other individual dose unit, the capsule or other unit can be opened and the contents emptied into a suitable vessel prior to dissolving.

The cysteamine formulation also can be a delayed release formulation such as an enteric-coated cysteamine formulation. To prepare delayed release cysteamine formulations such as enteric-coated cysteamine beads, the beads are generally ground to form a powder or are ground with an amount of a suitable solvent to form a paste. The resulting powder or paste is then dissolved to form a sample solution for analysis.

Enteric coatings prolong release until the cysteamine product reaches the intestinal tract, typically the small intestine. Because of the enteric coatings, delivery to the small intestine is improved thereby improving uptake of the active ingredient while reducing gastric side effects. Exemplary enterically coated cysteamine products are described in International Publication No. WO 2007/089670 published Aug. 9, 2007, which is incorporated in its entirety herein.

Generally, the enteric coating comprises a polymeric material that prevents cysteamine product release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a pKa in the range of about 3 to 5. Suitable enteric coating materials include, but are not limited to, polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit NE, Eudragit RL, Eudragit RS).

EXAMPLES

Example 1

Cysteamine bitartrate samples were assessed by gradient elution HPLC using an XBRIDGE C18 column (dimensions: 150 mm×4.6 mm; packing particle size: 3.5 μm) (Waters, Milford, Mass.). The autosampler temperature was 4° C. Approximately 10 μL or approximately 100 μL of sample was injected onto the column. The column temperature was 40° C. and the sample was eluted at a flow rate of 1.0 mL/min according to the following profile:

| | HPLC Gradient | |
| --- | --- | --- |
| Time (min) | Mobile Phase A (%) | Mobile Phase B (%) |
| 0.0 | 100 | 0 |
| 2.0 | 100 | 0 |
| 20.0 | 60 | 40 |

| HPLC Gradient | | |
|---|---|---|
| Time (min) | Mobile Phase A (%) | Mobile Phase B (%) |
| 25.0 | 60 | 40 |
| 25.1 | 100 | 0 |
| 40.0 | 100 | 0 |

Mobile Phase A contained 23.6 mM 1-octanesulfonic acid sodium and 29.0 mM sodium phosphate (pH 2.6)/acetonitrile/methanol 85/3/12 (v/v/v). Mobile Phase B contained 0.20 M 1-octanesulfonic acid sodium and 0.10 M sodium phosphate (pH 2.6)/acetonitrile/methanol 10/18/72 (v/v/v). The purity of 1-octanesulfonic acid was >98%. Detection was carried out using a UV detector at 210 nm.

Reference Solution Preparation. Reference solutions of Cysteamine Bitartrate Analytical Reference Standard were prepared as follows. Working Standard and Working Check Standard solutions were prepared having a nominal concentration of 0.54 mg/mL Cysteamine Bitartrate Analytical Reference Standard in Mobile Phase A using low actinic glassware. A Working Sensitivity solution was prepared having a nominal concentration of 0.30 mg/mL Cysteamine Bitartrate Analytical Reference Standard in Mobile Phase A using low actinic glassware, which corresponds to the limit of quantification (LOQ) for cysteamine. The water content of the Cysteamine Bitartrate Analytical Reference Standard was determined no more than 7 days before use by Karl Fischer titration or thermal gravimetric analysis (TGA). The Reference Standard was stored refrigerated and blanketed under nitrogen.

Bead Prep Assay Sample Preparation. Enteric-coated cysteamine (RP103) microbeads were prepared for analysis according to the following procedure. Enteric coated cysteamine formulation RP103 is described in co-owned application No. 61/835,965 (herein incorporated by reference). About 3.7 g of RP103 beads were ground to a fine powder using a ball mill for approximately 1 minute at 27 Hz. The grind was transferred to an amber bottle for storage. Stock Bead Prep Assay sample solutions were prepared in duplicate by adding 370.4 mg±5 mg of the grind to a 250 mL low actinic volumetric flask and diluting with Mobile Phase A. The mixture was stirred with a stir bar for at least 15 minutes. Approximately 15 mL of the resulting solution was filtered through a 0.45 μm nylon filter, with the first 5 mL being discarded. The cysteamine concentration of the resulting Stock Bead Prep Assay sample solution was approximately 0.300 mg/mL. Working Bead Prep sample solutions were prepared by placing 4.0 mL of Stock Bead Prep Assay sample solution in a 25 mL low actinic volumetric flask and diluting to volume with Mobile Phase A. The cysteamine concentration of the resulting Working Bead Prep sample solution was approximately 0.048 mg/mL.

Assay Sample Preparation. Capsules containing enteric-coated cysteamine (RP103) microbeads were prepared for analysis according to the following procedure. To reduce exposure to light and oxygen, sample preparation (from the initial weighing of the full capsules to the loading of sample vials on the HPLC) was completed in one day. Ten capsules were weighed. The capsule contents were emptied and the empty shells were weighed to determine the average capsule fill weight. The capsule contents were ground to a fine powder using a ball mill for approximately 1 minute at 27 Hz. The grind was transferred to an amber bottle for storage. Stock sample solutions were prepared in duplicate by adding the appropriate amount of the grind for 1 capsule (as determined by the average capsule fill weight) to a 25 mL low actinic volumetric flask and diluting with Mobile Phase A. The mixture was stirred with a stir bar for at least 15 minutes. The resulting solution was centrifuged at about 3400 rpm for 5 minutes. Approximately 15 mL of the centrifuged solution was filtered through a 0.45 μm nylon filter (Acrodisc, 25 mm diameter), with the first 5 mL being discarded, to obtain Stock sample solutions. Working sample solutions were prepared by placing 6.0 mL of Stock sample solution (for 25 mg capsules) or 2.0 mL of Stock sample solution (for 75 mg capsules) in a 10 mL low actinic volumetric flask and diluting to volume with Mobile Phase A.

Content Uniformity Sample Preparation. Capsules containing enteric-coated cysteamine (RP103) microbeads were prepared for analysis according to the following procedure. To reduce exposure to light and oxygen, sample preparation (from the initial weighing of the full capsules to the loading of sample vials on the HPLC) was completed in one day. Ten capsules were weighed. The contents of each capsule were emptied into separate mortars and the empty shells were weighed to determine the individual capsule fill weight. About 1-2 mL of Mobile Phase A was added into the mortar. The beads were immediately ground to a paste. If needed, additional Mobile Phase A was added to the paste, up to 5 mL total. The paste was transferred to a 250 mL low actinic volumetric flask. The mortar and pestle were thoroughly rinsed with Mobile Phase A and the rinse solution was collected in to the same flask. The flask was filled about three-quarters full with Mobile Phase A and stirred for at least 15 minutes. The flask was filled to volume with Mobile Phase A. Approximately 20 mL of the resulting solution was filtered through a 0.45 μm nylon filter (Acrodisc, 25 mm diameter), with the first 5 mL being discarded, to obtain Stock CU sample solutions. Working CU sample solutions were prepared by placing 12.0 mL of Stock CU sample solution (for 25 mg capsules) or 4.0 mL of Stock CU sample solution (for 75 mg capsules) in a 25 mL low actinic volumetric flask and diluting to volume with Mobile Phase A. The cysteamine concentration of the resulting Working CU sample solutions was approximately 0.048 mg/mL.

Data Analysis. The cysteamine Working Standard solution concentration was calculated according to the following equation: Cysteamine Concentration ($C_{Std}$)=mg Cysteamine Bitartrate Analytical Reference Standard×$P_f$/25.0 mL $P_f$ represents a purity factor for the standard material. $P_f$ was calculated according to the following equation: $P_f$=B×(100-Water)×C/100 where B=the anhydrous cysteamine free base in the Cysteamine Bitartrate Analytical Reference Standard (expressed as a decimal value on the standard bottle label), water=the water content as determined by Karl Fischer or TGA no more than 7 days before use (expressed as a percentage), and C=the cystamine correction (expressed as a decimal value on the standard bottle label).

The amount of cysteamine per capsule was calculated according to the following equation: mg cysteamine per capsule=($A_{Sam}$/$A_{Std}$)×$C_{Std}$×DF×(AveWt/SamWt)

where $A_{Sam}$=the peak area of cysteamine in the sample chromatogram with a 10 μL injection, $A_{Std}$=the average peak area of cysteamine in all Working Standard solution chromatograms with a 10 μL injection, $C_{Std}$=the concentration (mg/mL) of cysteamine in the Working Standard solution, DF=the dilution factor (125 for 75 mg capsules; 41.6667 for 25 mg capsules), AveWt=the average capsule fill weight (mg), and
SamWt=the sample weight (mg).

For Content Uniformity, the amount of cysteamine per capsule was calculated according to the following equation:
mg cysteamine per capsule= $(A_{Sam}/A_{Std}) \times C_{Std} \times DF$
where $A_{Sam}$=the peak area of cysteamine in the sample chromatogram with a 10 μL injection,
$A_{Std}$=the average peak area of cysteamine in all Working Standard solution chromatograms with a 10 μL injection,
$C_{Std}$=the concentration (mg/mL) of cysteamine in the Working Standard solution, and
DF=the dilution factor (1562.5 for 75 mg capsules; 520.8 for 25 mg capsules).

For the Bead Prep Assay, the amount of cysteamine per capsule was calculated according to the following equation:
mg cysteamine per capsule=$(A_{Sam}/A_{Std}) \times C_{Std} \times DF \times (AveWt/SamWt)$
where $A_{Sam}$=the peak area of cysteamine in the sample chromatogram with a 10 μL injection,
$A_{Std}$=the average peak area of cysteamine in all Working Standard solution chromatograms with a 10 μL injection,
$C_{Std}$=the concentration (mg/mL) of cysteamine in the Working Standard solution,
DF=the dilution factor (use the 75 mg Dilution Factor, 1562.5),
AveWt=the average capsule fill weight (mg) (use the target fill weight, 370.4 mg), and
SamWt=the sample weight (mg) (use the actual weight used in sample preparation).

The percentage of the label claim (% LC) was calculated for the Assay, Content Uniformity, and Bead Prep Assay sample solutions according to the following equation:

% LC=(mg cysteamine)/LC×100% where mg cysteamine=the amount calculated by the applicable equation above, and LC=the amount of the label claim (75 mg or 25 mg) (use 75 mg for the Bead Prep Assay).

The amount of substances related to cysteamine bitartrate (including cysteamine impurities) such as cystamine was calculated according to the following equation:

mg related substance=$(A_{RS}/A_{Std}) \times (C_{Std}/RRF) \times DF \times (AveWt/SamWt)$ where $A_{RS}$=the peak area of any related substance in the Working sample solution chromatogram with a 100 μL injection (peaks before RRT 0.48 were disregarded; peaks observed in the chromatogram of the second injection of Mobile Phase A/Blank (100 μL injection) were also disregarded),
$A_{Std}$=the average peak area of cysteamine in all Working Standard solution chromatograms with a 10 μL injection,
$C_{Std}$=the concentration (mg/mL) of cysteamine in the Working Standard solution,
RRF=the relative response factor (0.98 for cystamine; 1.00 for other related substances),
DF=the dilution factor (12.5 for 75 mg capsules; 4.16667 for 25 mg capsules),
AveWt=the average capsule fill weight (mg), and
SamWt=the weight the sample grind from the Working sample solution preparation (mg).

The weight percentage of cystamine and other individual related substances was determined according to the following equation:

% individual related substance=mg related substance/mg cysteamine×100% where mg related substance=the amount of related substance calculated above, and mg cysteamine=the amount of cysteamine for the Assay sample.

The percentage of total related substances was determined by summing all related substances greater than or equal to 0.05%. Peaks after 28 minutes were disregarded. In contrast to a previous electrochemical detection method that disregarded early-eluting peaks as not relevant to the purity calculation, the foregoing method determines that early peaks are impurities and integrates early-eluting peaks as described above.

Five lots of enteric-coated cysteamine (RP103) (delayed release, 75 mg strength) and two lots of cysteamine without an enteric-coating (Cystagon®) (immediate release) were tested according to the procedure described above to determine the weight percentage of related substances. The five RP103 batches were tested at the time of lot release ("Time 0") and at 12 or 18 months after lot release. The percentage of each related substance was calculated as a weight percentage of cysteamine. An RRF of 1.00 was assigned to each related substance (except for cystamine) because a sufficient quantity of the related substances to determine RRF was not isolated. For cystamine, RRF was determined to be 0.98. The results of testing are provided in Table 1 and a representative chromatogram is provided in FIG. 1.

TABLE 1

| Related Substance Peak No. | Relative Retention Time (RRT) | RP103 Lot 1 | | RP103 Lot 2 | | RP103 Lot 3 | |
|---|---|---|---|---|---|---|---|
| | | Time 0 | 18 mo. | Time 0 | 18 mo. | Time 0 | 18 mo. |
| Cystamine | n/a | 3.2 | 4.2 | 3.4 | 4.1 | 3.2 | 3.8 |
| A | 0.48-0.52 | | | | | | |
| B | 0.55-0.56 | <0.05 | | | 0.21 | | 0.19 |
| C | 0.67-0.69 | | | | 0.08 | | 0.07 |
| 3 | 0.78-0.82 | 0.17 | 0.13 | 0.18 | 0.16 | 0.14 | 0.14 |
| 1 | 0.83-0.86 | 0.35 | 0.71 | 0.30 | 0.49 | 0.31 | 0.46 |
| D | 0.87-0.90 | | 0.13 | | | | |
| 2 | 0.91-0.94 | 0.09 | 0.94 | 0.09 | 1.1 | 0.09 | 1.1 |
| 4 | 0.95-0.97 | | 0.09 | | 0.22, 0.06 | | 0.22, 0.06 |
| 5 | 1.13-1.16 | | 0.14 | | 0.17 | | 0.16 |
| E | 1.25-1.26 | | | | | | |
| 6 | 1.30-1.34 | | 0.19 | | 0.21 | | 0.21 |
| F | 1.51-1.54 | 0.05 | | 0.07 | | 0.06 | |
| G | 1.59-1.63 | 0.07 | | | | | |
| H | 1.64-1.65 | 0.09 | | 0.12 | | 0.11 | |
| I[§] | 1.72-1.73 | | | | 1.0[§] | | 1.0[§] |
| J | 1.98-2.01 | | 0.12 | | | | |

TABLE 1-continued

| | | | | | | | |
|---|---|---|---|---|---|---|---|
| K | 2.39-2.41 | | 0.08 | | | | |
| Individual Unspecified Peak | | | 0.93, 0.10% 1.39, 0.06% 1.93, 0.06% 2.16, 0.07% 2.20, 0.05% | 1.56, 0.05% | 1.77, 0.05% | | |
| Total Related Substances | | 4.0 | 7.1 | 4.2 | 6.8 (without Peak I) | 3.9 | 6.4 (without Peak I) |

| Related Substance | RP103 Lot 4 | | RP103 Lot 5 | | Cystagon ® Lot 1 | Cystagon ® Lot 2 |
|---|---|---|---|---|---|---|
| Peak No. | Time 0 | 12 mo. | Time 0 | 12 mo. | Not available | Not available |
| Cystamine | 3.7 | 3.7 | 3.6 | 3.3 | 9.1 | 5.2 |
| A | 0.14 | | 0.13 | | | 0.07 |
| B | | 0.06 | | 0.08 | 0.09 | 0.10 |
| C | | | | | | |
| 3 | 0.06 | 0.10 | 0.07 | 0.11 | 0.09 | |
| 1 | 0.21 | 0.45 | 0.20 | 0.50 | 0.31 | 0.20 |
| D | | | | | | |
| 2 | 0.06 | 0.71 | 0.06 | 0.75 | 0.15 | |
| 4 | | 0.08 | | 0.07 | | |
| 5 | | 0.10 | | 0.08 | 0.07 | |
| E | | | | | 0.11 | |
| 6 | | 0.09 | | 0.07 | 0.14 | 0.07 |
| F | | | | | 0.07 | |
| G | 0.06 | 0.11 | 0.11 | | 0.09 | 0.07 |
| H | | | | | | |
| I§ | | | | | 0.07 | |
| J | | | | | | |
| K | | | | | | |
| Individual Unspecified Peak | | | | 1.39, 0.06% | | |
| Total Related Substances | 4.2 | 5.4 | 4.2 | 5.0 | 10.3 | 5.7 |

§Peak I is believed to be a contaminant and was not observed in samples analyzed on other days.

These results demonstrate lower total related substances for enteric-coated cysteamine at the time of lot release and at 12 months after lot release relative to cysteamine without an enteric-coating. For example, the present method shows that lots of an immediate release cysteamine formulation comprise over 5% cystamine impurity whereas it was previously shown by an electrochemical detection method that the immediate release product comprised less than 5% cystamine impurity. In contrast, the method shows that the delayed release composition RP103 comprises less than 5% cystamine impurity. Further, using the UV detection method additional impurity peaks, for example, Peak 1, Peak 5, and Peak 6 (see Table 1 and FIG. 1), were detectable, which were not detected by an electrochemical detection method. These results also demonstrate that the present methods provides highly sensitive and accurate determination of related substances present in the cysteamine formulations.

Example 2

UV detection of cysteamine bitartrate impurities was compared to electrochemical detection, which has been used previously to detect impurities in an immediate release formulation of cysteamine. Two cysteamine bitartrate samples (without an enteric coating) were assessed by HPLC. The first sample (Sample A) contained cysteamine bitartrate (CBT) at a concentration of 1 mg/mL, spiked with thiomorpholine (TMP), thiomorpholine-1-oxide (OTMP), Peak 1 (see Table 1 and FIG. 1) (RRT0.85), and Peak 4 (see Table 1 and FIG. 1) (R4). The second sample (Sample B) contained cysteamine bitartrate (CBT) at a concentration of 1 mg/mL, spiked with lanthionamine (TBEA), Peak 5 (see Table 1 and FIG. 1) (R5), Peak 6 (see Table 1 and FIG. 1) (R6), and Peak D (see Table 1) (RRT0.89). Both samples were stored at 5° C. for a few days prior to HPLC analysis.

Samples A and B were assessed by isocratic elution HPLC using an ATLANTIS T3 C18 column (dimensions: 150 mm×4.6 mm; packing particle size: 3 μm) (Waters, Milford, Mass.). The autosampler temperature was 5° C. Approximately 10 μL of sample was injected onto the column. The column temperature was 40° C. and the sample was eluted at a flow rate of 1.0 mL/min for 15 minutes. The mobile phase contained 8.8 mM sodium hexanesulfonate monohydrate, 0.1% $H_3PO_4$ in 88/12 water/acetonitrile (v/v). The needle was washed with water.

UV detection was carried out using a UV detector at 200 nm. Electrochemical detection was carried out using an electrochemical detector with a condition cell (250 mV, 5 μA) and an analytical cell (650 mV, 100 μA).

Figure 2:
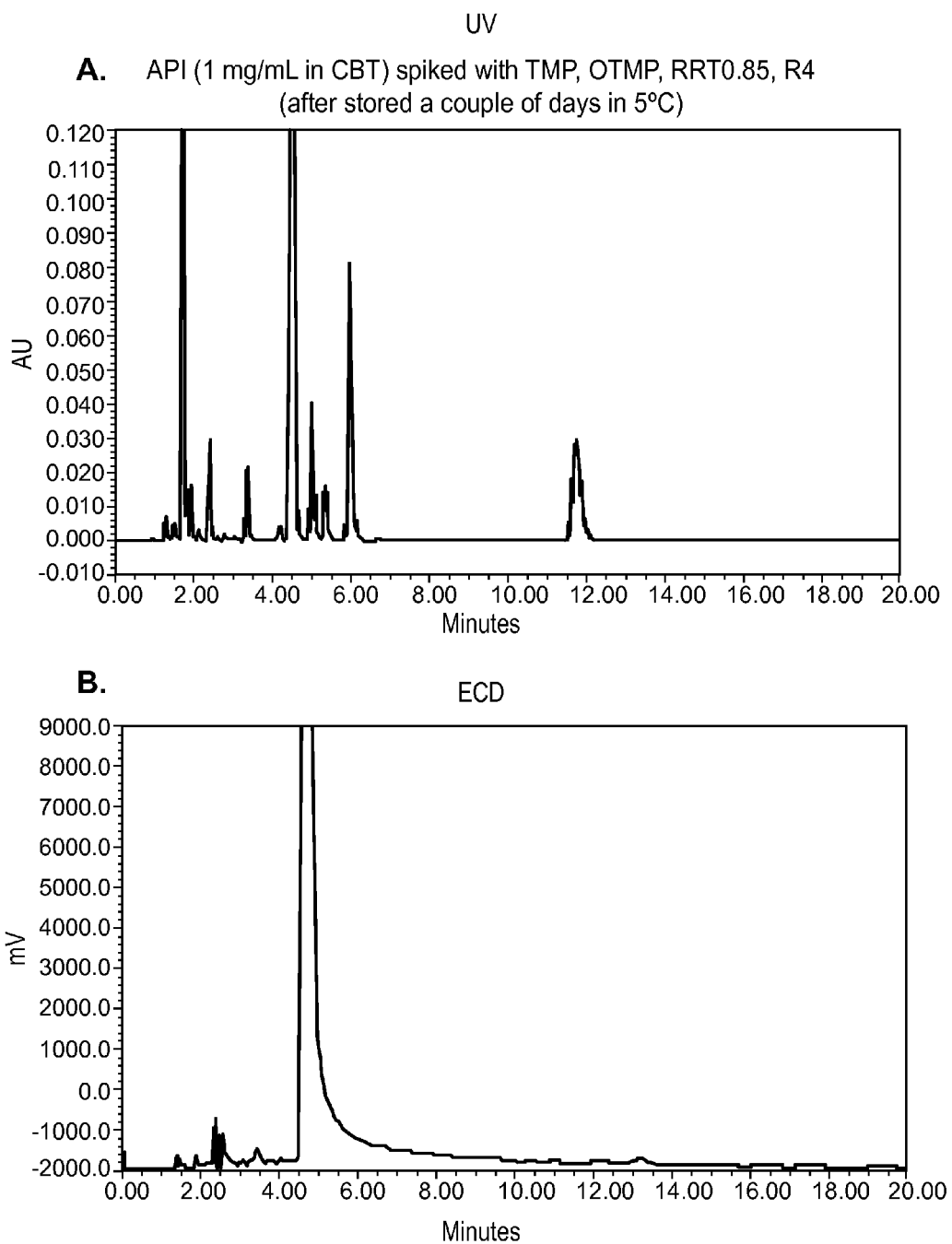
FIG. 2 provides HPLC chromatograms of cysteamine from Sample A obtained using a UV detector (A) and using an electrochemical detector (B).
Figure 3:
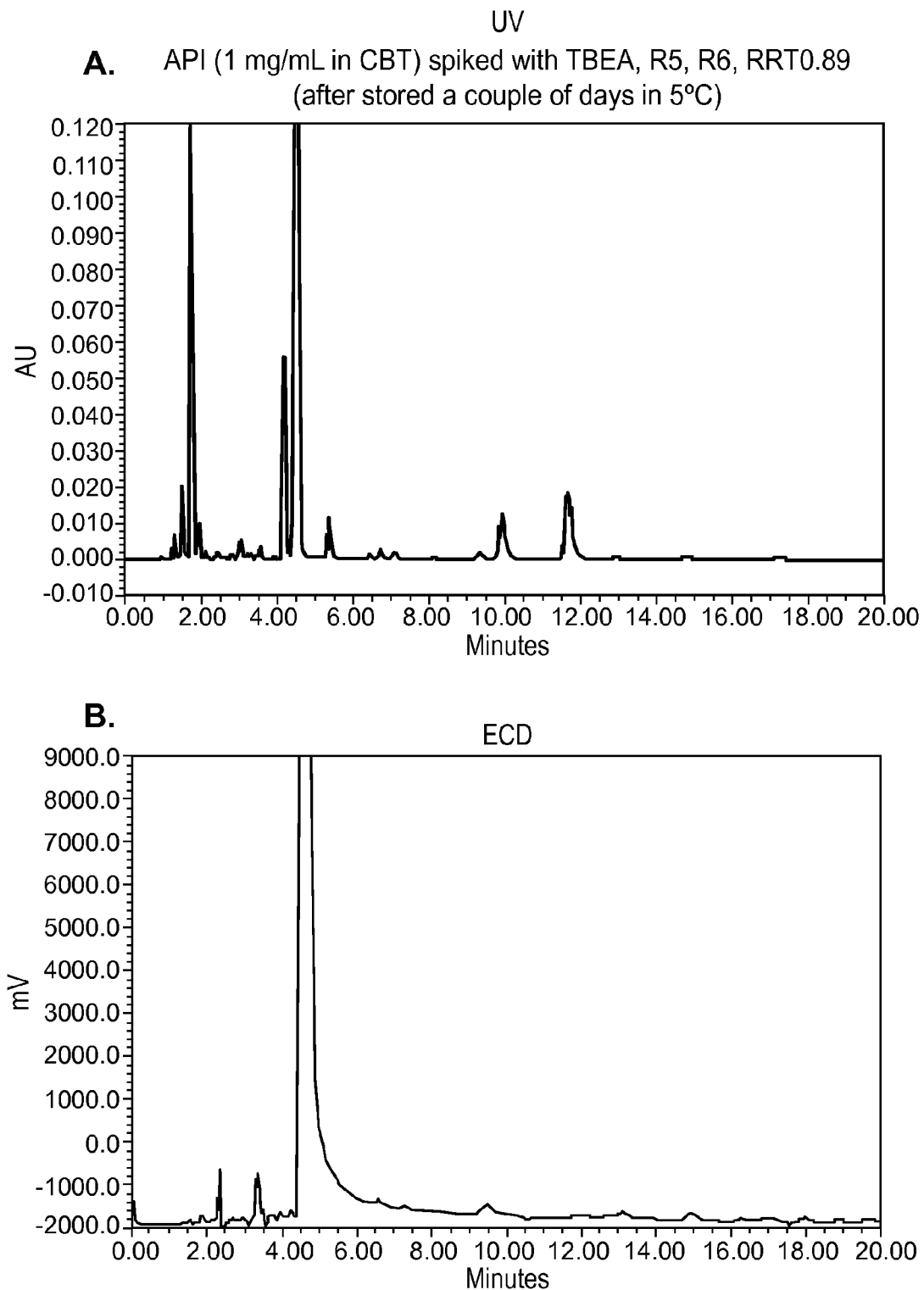
FIG. 3 provides HPLC chromatograms of cysteamine from Sample B obtained using a UV detector (A) and using an electrochemical detector (B).

Electrochemical detection was initially thought to be a more sensitive detection method compared to UV detection. However, as shown in FIG. 2 and FIG. 3, additional peaks were detected and greater peak resolution was demonstrated by the UV detection method described herein (A) as compared to the electrochemical detection method (B). FIG. 2 corresponds to Sample A and FIG. 3 corresponds to Sample B.

Without intending to be bound by theory, it is believed that many of the impurities identified herein and detected using the UV detector at low wavelength do not undergo a redox reaction, which is necessary for an impurity to be detected using an electrochemical detector. Therefore, as illustrated below, the UV detection method identifies more impurity peaks than an electrochemical detection method.

For example, the UV detection method identified additional impurity peaks not identified by electrochemical detection, such as thiomorpholine (TMP), thiomorpholine-1-oxide (OTMP), Peak D, Peak 4, lanthionamine (TBEA), Peak 5, and Peak 6.

Thus, the UV detection method described herein demonstrated higher sensitivity and less selectivity compared to electrochemical detection.

What is claimed is:

1. A method of analyzing purity of a composition comprising cysteamine comprising:
    (i) injecting a sample solution comprising cysteamine onto a reverse-phase HPLC column;
    (ii) eluting the sample from the column using a mobile phase comprising an alkyl sulfonic acid, a buffer, acetonitrile, and methanol; and
    (iii) measuring the eluted sample using a UV detector at a wavelength of about 170 nm to about 250 nm;
    wherein the sample is eluted using a gradient elution, the elution comprising gradient eluting the sample using first and second mobile phases,
    wherein the first mobile phase comprises:
    about 75% to about 95% by volume of an aqueous solution having a pH of about 2.0 to 3.0, the aqueous solution comprising an alkyl sulfonic acid and a phosphate buffer,
    about 1% to about 8% by volume of acetonitrile, and
    about 5% to about 20% by volume of methanol; and
    the second mobile phase comprises:
    about 5% to about 30% by volume of an aqueous solution having a pH of about 2.0 to 3.0, the aqueous solution comprising an alkyl sulfonic acid and a phosphate buffer,
    about 8% to about 30% by volume of acetonitrile, and
    about 50% to about 85% by volume of methanol.

2. The method of claim 1, further comprising dissolving a cysteamine sample in a solvent having an acidic pH to form the sample solution comprising cysteamine.

3. A method of analyzing purity of enteric-coated cysteamine beads comprising:
    (i) grinding enteric-coated cysteamine beads;
    (ii) dissolving the ground beads in a solvent having an acidic pH to form a sample solution comprising cysteamine;
    (iii) injecting the sample solution onto a reverse-phase HPLC column;
    (iv) eluting the sample from the column using a mobile phase comprising an alkyl sulfonic acid, a buffer, acetonitrile, and methanol; and
    (v) measuring the eluted sample using a UV detector at a wavelength of about 170 nm to about 250 nm;
    wherein the sample is eluted using a gradient elution, the elution comprising gradient eluting the sample using first and second mobile phases,
    wherein the first mobile phase comprises:
    about 75% to about 95% by volume of an aqueous solution having a pH of about 2.0 to 3.0, the aqueous solution comprising an alkyl sulfonic acid and a phosphate buffer,
    about 1% to about 8% by volume of acetonitrile, and
    about 5% to about 20% by volume of methanol; and
    the second mobile phase comprises:
    about 5% to about 30% by volume of an aqueous solution having a pH of about 2.0 to 3.0, the aqueous solution comprising an alkyl sulfonic acid and a phosphate buffer,
    about 8% to about 30% by volume of acetonitrile, and
    about 50% to about 85% by volume of methanol.

4. The method of claim 2 or 3, wherein the solvent comprises an alkyl sulfonic acid, a buffer, acetonitrile, and methanol.

5. The method of claim 1 or 3, wherein the HPLC column has a packing material particle size of about 1 μm to about 10 μm in diameter.

6. The method of claim 1 or 3, wherein the HPLC column has an internal diameter of about 0.1 mm to about 10 mm.

7. The method of claim 1 or 3, wherein the eluted sample is measured using a UV detector at a wavelength of about 180 nm to about 230 nm.

8. The method of claim 1 or 3, wherein the aqueous solution of the first mobile phase comprises:
    about 15 mM to about 50 mM of an alkyl sulfonic acid, and
    about 15 mM to about 100 mM phosphate buffer.

9. The method of claim 1 or 3, wherein the aqueous solution of the second mobile phase comprises:
    about 100 mM to about 300 mM of an alkyl sulfonic acid, and
    about 100 mM to about 200 mM phosphate buffer.

10. The method of claim 1 or 3, wherein the sample is eluted using a flow rate of about 0.001 mL/min to about 2 mL/min.

11. The method of claim 1 or 3, wherein the sample solution comprises cysteamine bitartrate.

12. The method of claim 3, wherein the beads are ground to form a powder.

13. The method of claim 3, wherein the beads are ground to form a paste.

14. A method of analyzing purity of compositions comprising cysteamine comprising:
    (i) dissolving a cysteamine sample in a solvent having an acidic pH to form a sample solution comprising cysteamine;
    (ii) injecting the sample solution onto a C18 reverse-phase HPLC column;
    (iii) gradient eluting the sample from the column using first and second mobile phases,
    wherein the first mobile phase comprises: about 85% by volume of an aqueous solution having a pH of about 2.6, the aqueous solution comprising about 23.6 mM 1-octanesulfonic acid sodium and about 29 mM sodium phosphate; about 3% by volume of acetonitrile; and about 12% by volume of methanol, and
    the second mobile phase comprises: about 10% by volume of an aqueous solution having a pH of about 2.6, the aqueous solution comprising about 0.2 M 1-octanesulfonic acid sodium and about 0.1 M sodium phosphate; about 18% by volume of acetonitrile; and about 72% by volume of methanol; and
    (iv) measuring the eluted sample using a UV detector at a wavelength of about 210 nm or less.

15. The method of claim 14, comprising gradient eluting at a flow rate of about 1.0 mL/min according to the following profile:

| | HPLC Gradient | |
|---|---|---|
| Time (min) | First Mobile Phase (%) | Second Mobile Phase (%) |
| 0.0 | 100 | 0 |
| 2.0 | 100 | 0 |
| 20.0 | 60 | 40 |
| 25.0 | 60 | 40 |
| 25.1 | 100 | 0 |
| 40.0 | 100 | 0 |

16. The method of claim 14, wherein the HPLC column has a packing material particle size of about 3.5 μm in diameter.

17. The method of claim 14, wherein the HPLC column has a length of about 150 mm and an internal diameter of about 4.6 mm.

18. The method of any one of claim 1, 3, or 14, comprising injecting at least 30 μg of cysteamine onto the column.

* * * * *